US011883516B2

(12) United States Patent
Bapat et al.

(10) Patent No.: US 11,883,516 B2
(45) Date of Patent: Jan. 30, 2024

(54) HIGH SPF SKIN CLEANSING COMPOSITION

(71) Applicant: CONOPCO, INC., Englewood Cliffs, NJ (US)

(72) Inventors: Mohini Anand Bapat, Mumbai (IN); Praful Gulab Rao Lahorkar, Bangalore (IN); Rajkumar Perumal, Erode District (IN); Nikita Tomar, Nagpur (IN); Ashish Anant Vaidya, Bangalore (IN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 17/925,846

(22) PCT Filed: May 31, 2021

(86) PCT No.: PCT/EP2021/064527
§ 371 (c)(1),
(2) Date: Nov. 17, 2022

(87) PCT Pub. No.: WO2021/245018
PCT Pub. Date: Dec. 9, 2021

(65) Prior Publication Data
US 2023/0181439 A1 Jun. 15, 2023

(30) Foreign Application Priority Data

Jun. 2, 2020 (IN) .............................. 202021023193
Jul. 15, 2020 (EP) ..................................... 20185857

(51) Int. Cl.
*A61K 8/49* (2006.01)
*A61K 8/46* (2006.01)
*A61Q 17/04* (2006.01)
*A61Q 19/10* (2006.01)

(52) U.S. Cl.
CPC ............ *A61K 8/4946* (2013.01); *A61K 8/466* (2013.01); *A61Q 17/04* (2013.01); *A61Q 19/10* (2013.01); *A61K 2800/592* (2013.01)

(58) Field of Classification Search
None
See application file for complete search history.

(56) References Cited

U.S. PATENT DOCUMENTS

| 2,798,053 | A | 7/1957 | Brown |
| 4,585,597 | A | 4/1986 | Lang et al. |
| 11,491,088 | B2 * | 11/2022 | Traynor .................. A61K 8/466 |
| 2005/0158268 | A1 | 7/2005 | Schmucker-Castner et al. |
| 2005/0239669 | A1 | 10/2005 | Krzysik et al. |
| 2005/0265936 | A1 | 12/2005 | Knopf et al. |
| 2007/0041930 | A1 | 2/2007 | Meder et al. |
| 2007/0110686 | A1 | 5/2007 | Lowe et al. |
| 2008/0075684 | A1 | 3/2008 | Barg et al. |
| 2008/0112904 | A1 | 5/2008 | Traynor et al. |
| 2008/0194708 | A1 | 8/2008 | Hossel et al. |
| 2010/0209363 | A1 | 8/2010 | Ge et al. |
| 2011/0020251 | A1 | 1/2011 | Shih et al. |
| 2018/0042828 | A1 | 2/2018 | Cohen |
| 2018/0296455 | A1 | 10/2018 | Blachechen et al. |

FOREIGN PATENT DOCUMENTS

| EP | 1261688 | 5/2005 |
| EP | 2939710 | 11/2015 |
| WO | WO0018367 | 4/2000 |
| WO | WO0064406 | 11/2000 |
| WO | WO0168036 | 9/2001 |
| WO | WO2006083843 | 8/2006 |
| WO | WO2017110152 | 6/2017 |
| WO | WO2017110153 | 6/2017 |
| WO | WO2019108198 | 6/2019 |
| WO | WO2021245082 | 12/2021 |

OTHER PUBLICATIONS

IPRP1 in PCTEP2021064678; Dec. 15, 2022; World Intellectual Property Org. (WIPO).
GNPD Database (Online) Mintel; Elegant Sua Tam (Shower Cream); Aquala; Mar. 2017; pp. 1-2, Record ID 4649621; Vietnam.
GNPD Database (Online) Mintel; Sua Tam (Orange Ginger Shower Cream); Aquala; Jun. 2017; pp. 1-2, Record ID: 4898671; Vietnam.
GNPD Database (Online) Mintel; abón Corporal + Baño de Espuma Manzanilla Negra (Body Wash & Foam Bath); Bath & Body Works Aromatherapy Sleep Black Chamomile; Aug. 2019; pp. 1-2, Record ID: 6761487; Colombia.
GNPD Database (Online) Mintel; Gel' dlya Dusha dlya Utonchennykh Natur (Shower Gel for Refined Ladies); Fa Festival Glam; Jul. 2019; pp. 1-2, Record ID: 6741419; Russian Federation.
GNPD Database (Online) Mintel; 2 in 1 Hair and Body Wash; Ginvera Kids; Aug. 2006; pp. 1-2, Record ID: 571768; Malaysia.
GNPD Database (Online) Mintel; Happy Body Wash; Ginvera Kids; Jun. 2016; pp. 1-2, Record ID: 4093115; Malaysia.
GNPD Database (Online) Mintel; Jabón Líquido para Manos & Cuerpo (Hands & Body Liquid Soap); Karina Rabolini; Jul. 2017; pp. 1-2, Record ID: 4965707; Argentina.
GNPD Database (Online) Mintel; Lavender Aromachology UV Whitening Shower Scrub; Nuolive Spa Series; Feb. 2011; pp. 1-2, Record ID: 1486649; Vietnam.

(Continued)

Primary Examiner — Nannette Holloman
(74) Attorney, Agent, or Firm — Krista J. Aiello

(57) ABSTRACT

The invention relates to a personal cleansing composition that delivers enhanced deposition of sunscreens on to the topical surface of the body. The composition more particularly provides for such wash off compositions that ensure that the sunscreens incorporated therein are stable and due to the high deposition on to surface provide high Sun Protection Factor (SPF). This is achieved through combination of two select water-soluble sunscreens in a high surfactant containing composition.

8 Claims, No Drawings

(56) References Cited

OTHER PUBLICATIONS

GNPD Database (Online) Mintel; Seaweed Relaxing Deep Sea UV Whitening Shower Scrub; Nuolive Spa Series; Sep. 2011; pp. 1-2, Record ID: 1621801; Vietnam.
GNPD Database (Online) Mintel; Sua Tam Oliu (Olive Shower Gel); Oliv de Prôvence; Jun. 2017; pp. 1-2, Record ID: 4880191; Vietnam.
GNPD Database (Online) Mintel; Shower Oil; Sabon Citrus Blossom; Mar. 2017; pp. 1-2, Record ID: 4701051; Israel.
GNPD Database (Online) Mintel; Shower Oil; Sabon Delicate Jasmine; Jun. 2018; pp. 1-2, Record ID: 5721699; Israel.
GNPD Database (Online) Mintel; Shower Oil; Sabon Rose Splash; Feb. 2019; pp. 1-2, Record ID: 6361939; Israel.
GNPD Database (Online) Mintel; Bain Corps & Cheveux (Hair & Body Bath); Schwarzkopf Professional BC Bonacure Sun Protect; Jul. 2019; pp. 1-2, Record ID: 6746323; France.
GNPD Database (Online) Mintel; Body Shower Gel; Universo Garden Angels Lovers; Apr. 2009; pp. 1-2, Record ID: 1072856; Argentina.
Search Report and Written Opinion in EP20185857; dated Nov. 25, 2020; European Patent Office (EPO).
Anonymous; Cosmetic compositions comprising Polyquaternium-74 copolymer ED—Darl Kuhn; IP.com Technical Disclosure; Nov. 28, 2007; pp. 1-116, XP013122962; Centre de Recherches d'Aubervilliers; United States of America.
Final Report on the Safety Assessment of Benzophenones-1, -3, -4, -5, -9, and -11; Journal of the American College of Toxicology; Jan. 1, 1983; pp. 35-77, XP055749572; vol. 2 No 5; Mary Ann Liebert, Inc.
Anonymous; Technical Data Sheet MFSORB 103; MFCI UVAbsorvers Specialist; May 1, 2015; pp. 1-3, XP055749581, Retrieved from the Internet: URL:http://www.uni-trading.com/sub/support/tds.msds/additive/UV/TDS/BP-9%20TDS(EN).pdf;.
Search Report and Written Opinion in EP20185852; dated Nov. 23, 2020; European Patent Office (EPO).
Search Report and Written Opinion in PCTEP2021064527; dated Aug. 30, 2021; World Intellectual Property Org. (WIPO).
Search Report and Written Opinion in PCTEP2021064678; dated Aug. 31, 2021; World Intellectual Property Org. (WIPO).
IPRP2 in PCTEP2021064527; Sep. 13, 2022; World Intellectual Property Org. (WIPO).
Symrise; disodium 2-[4-(4,6-disulfobenzimidazol-3-id-2-yl)phenyl]benzimidazol-3-ide-4,6-disulfonic acid; disodium phenyl dibenzimidazole tetrasulfonate neo heliopan AP; 2023; pp. 1-5, Retrieved from the Internet: URL: https://www.thegoodscentscompany.com/data/rw1647421.html; Code 164742, CAS No. 180898-37-7; The Good Scents Company.

* cited by examiner

HIGH SPF SKIN CLEANSING COMPOSITION

CROSS REFERENCE TO RELATED APPLICATIONS

The present application is a U.S. National Phase Application under 35 U.S.C. § 371 of International Application No. PCT/EP2021/064527, filed on May 31, 2021, which claims priority to International Application No. PCT/IN2020/21023193, filed on Jun. 2, 2020, and European Patent Application No. 20185857.8, filed on Jul. 15, 2020, the contents of which are incorporated herein in their entireties.

FIELD OF THE INVENTION

The invention relates to a personal cleansing composition that delivers enhanced deposition of sunscreens on to the topical surfaces of the body. The composition more particularly provides for such wash off compositions that ensure that the sunscreens incorporated therein are stable and due to the high deposition on to skin, provide high Sun Protection Factor (SPF).

BACKGROUND OF THE INVENTION

Solar radiation includes about 5% ultraviolet (UV) radiation, wavelength of which is between 200 nm and 400 nm. It is further classified into three regions: from 320 to 400 nm (UVA), 290 to 320 nm (UVB) and from 200 to 290 nm (UVC). Exposure to UVA and UVB radiation for short period is known to cause reddening of the skin and localized irritation. Continued and prolonged exposure can lead to sunburn, melanoma and formation of wrinkles. It is also reported that UV radiation causes significant damage to hair. Therefore, people desire to protect their skin and hair from the harmful effects of both UVA and UVB radiation.

Various cosmetic preparations that one can apply on to the skin as creams, lotions or gels have been reported for preventing and/or protecting the skin from harmful effects of UV radiation. These cosmetic compositions usually comprise different types of organic sunscreen agents, especially ones capable of absorbing the UVA and/or UVB radiation present in the sun's rays. Thus, both UVA and UVB sunscreens are usually incorporated so as to provide protection over the entire range of UV radiation. Such leave-on compositions are applied on to skin before a person goes outdoors and they remain thereon till the person has a next wash. The problem with leave-on compositions is that the person has to spend some time before going out, applying the product on to the skin. In addition to being time-consuming, leave-on compositions are generally delivered through a cream, lotion or gel. Some people may not like the sensorial properties of the product being applied on the skin. An alternate method of application of sunscreens on the skin is through wash-off products like soaps, face wash or body wash products where the sunscreens are incorporated in the skin cleansing products and are delivered on to the skin concurrent with the washing process. However, it is an extremely difficult challenge to deliver sunscreens on to skin when the primary purpose of wash-off products is to remove the dirt and oils from the skin surface and together with that, the actives in the wash-off products are also highly likely to get washed away. Thus, enhanced deposition of actives through wash-off products is an on-going challenge.

The present inventors with their years of experience in understanding the nature of available sunscreens; the knowledge of interfacial science of surfactant systems and through extensive experimentation set out find a solution to the problem of delivering UV protection through delivering high SPF on to skin through wash off products.

EP1261688 (Unilever, 2001) discloses a personal wash composition which deposit high levels of sunscreen (SPF>2) while maintaining good lather (i.e. suffer minimal lather degradation over time relative to compositions with more "oily" sunscreens). Enhanced deposition is found from both bar and liquid compositions and is based on the solubility or non-solubility of the sunscreen used.

The present inventors have found that there is a limit to the SPF that can be achieved with the invention disclosed in prior art. Incorporation of higher amounts of sunscreens as taught in prior art did not provide for any enhancement in the deposition efficacy and thereby the SPF achieved.

By way of the present invention, it has been determined that it is necessary to combine two different types of sunscreens (one which provides predominantly UVA protection and the other which predominantly provides UVB protection) in order to get enhanced and even synergistic SPF benefits.

It is therefore an object of the present invention to obviate at least some drawbacks of the prior art and provide a personal cleansing composition which delivers enhanced SPF as compared to the known art.

SUMMARY OF THE INVENTION

According to the first aspect of the present invention, there is provided a personal cleansing composition for enhanced deposition of sunscreens on the topical surface of the body comprising:
  (a) 0.1 to 10 wt % of a water soluble UVA sunscreen;
  (b) 0.1 to 10 wt % of a water soluble UVB sunscreen;
  (c) 3 to 80 wt % surfactant; and
  (d) a cosmetically acceptable carrier,
  wherein the water soluble UVA sunscreen is selected from di sodium phenyl dibenzimidazole tetra sulfonate, terephthalylidene dicamphor sulfonic acid and mixtures thereof, and
  wherein the water soluble UVB sunscreen is selected from phenyl benzimidazole sulphonic acid, benzylidene camphor sulfonic acid, benzophenone-4 and mixtures thereof, and
  wherein the solubility in water of said UVA sunscreen and said UVB sunscreen is higher than 10 g/L at 25° C.

The second aspect of the present invention relates to a method of providing improved sun protection factor to a topical surface from a wash off composition comprising the steps of:
  (a) washing the surface with a composition of the first aspect, preferably diluted with water; and
  (b) rinsing said surface with water,
  wherein the sun protection factor is at least 8.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Unless specified otherwise, amounts as used herein are expressed in percentage by weight based on total weight of the composition and is abbreviated as "wt %".

Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

The disclosure of the invention as found herein is to be considered to cover all embodiments as found in the claims as being multiply dependent upon each other irrespective of the fact that claims may be found without multiple dependency or redundancy. Where a feature is disclosed with respect to a particular aspect of the invention (for example a composition of the invention), such disclosure is also to be considered to apply to any other aspect of the invention (for example a method of the invention) mutatis mutandis.

By "a personal cleansing composition" as used herein, is meant to include a composition for cleaning topical surfaces of mammals, especially humans. This composition is particularly useful for use on the sun-exposed parts of the body. Such a composition is generally of the rinse off type which means that the composition is high in surfactants which are known to help in cleaning surfaces to make them free of oils and dirt. The composition is generally used by diluting with water as it is applied on to skin, scalp or hair, after which the consumer works up a lather to ensure that the dirt and oil on the surface are solubilized in the micelles of the surfactant solution and the body is then rinsed with copious amounts of water to ensure that the surface is substantially free of the composition. The composition of the present invention can be in the form of a liquid, lotion, cream, gel, shampoo, conditioner or soap bar. "Skin" as used herein is meant to include skin on the face and body (e.g. neck, chest, back, arms, underarms, hands, legs, buttocks and scalp) and especially to the sun exposed parts thereof. The composition of the invention is also of relevance to application on any other keratinous substrates of the human body other than skin e.g. scalp and hair where products may be formulated with specific aim of providing UV protection. The unique benefit of the present invention is that while the surfactant in the composition along with the dirt and oil on the skin surface are substantially removed during the washing and rinsing process, it was surprisingly observed that the specific combination of the sunscreens ensures that they deposit in much higher amounts than is generally expected from rinse off products. The enhanced deposition leads to delivering high Sun Protection Factor (SPF). By high SPF as per this invention is meant a composition that has an SPF higher than 8, preferably higher than 10. The SPF in the present invention is measured using transmittance measurement technique.

The present invention relates to a personal cleansing composition for enhanced deposition of sunscreens on skin comprising a water-soluble UVA sunscreen; a water soluble UVB sunscreen; 3 to 80 wt % surfactant; and a cosmetically acceptable carrier. By water soluble sunscreen, whether of the UVA type, or of the UVB type, is meant that the solubility in water of the sunscreen is higher than 10 g/L preferably higher than 50 g/L at 25° C.

The water soluble UVB sunscreen for use in the present invention is selected from phenyl benzimidazole sulphonic acid (PBSA), benzylidene camphor sulfonic acid, benzophenone-4 and mixtures thereof. Preferably, the water soluble UVB subscress is PBSA.

PBSA has the chemical structure:

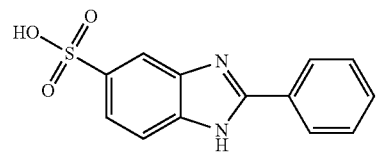 [SMILES: O=S(=O)(O)c1ccc2[nH]c(-c3ccccc3)nc2c1]

2-Phenylbenzimidazole 5-sulfonic acid

PBSA also known as Ensulizole is commercially available as Eusolex 232 (from Merck KGaA). PBSA is also available under the brand names Neo Heliopan Hydro (from Symrise), Parsol HS (from DSM) and Sunsafe ES (from Uniproma).

Benzylidene camphor sulfonic acid has the chemical structure:

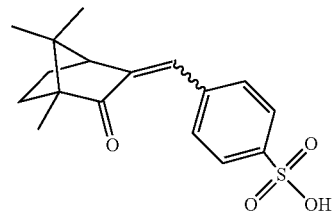 [SMILES: CC12CCC(C(=Cc3ccc(S(=O)(=O)O)cc3)C1=O)C2(C)C]

Benzophenone-4 (Sulisobenzone) has the chemical structure:

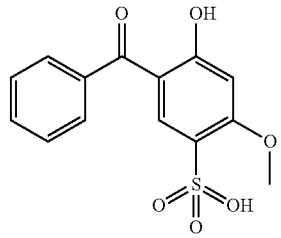

Benzophenone-4 is known to provide both, a UVA screening efficacy as well as a UVB screening efficacy. However, for the purposes of the present invention, Benzophenone-4 is used as UVB water soluble sunscreen.

The water soluble UVA sunscreen for use in the present invention is selected from disodium phenyl dibenzimidazole tetrasulfonate (Neoheliopan AP), terephthalylidene dicamphor sulfonic acid (TDSA) and mixtures thereof.

Di sodium phenyl dibenzimidazole tetra sulfonate also known as bisdisulizole disodium has the chemical structure as given below:

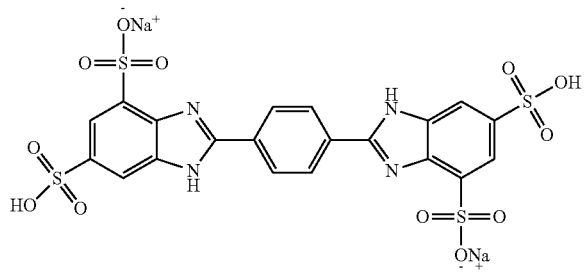

This is commercially available as Neo heliopan AP (from Symrise Shanghai Ltd) or as Sunsafe DPDT (from Uniproma)

Terephthalylidene dicamphor sulfonic acid (TDSA) has the structure

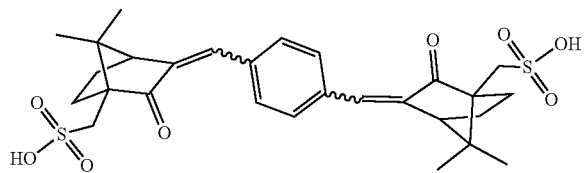 [SMILES: CC1(C)C2CCC1(CS(=O)(=O)O)C(=O)C2=Cc1ccc(C=C2C(=O)C3(CS(=O)(=O)O)CCC2C3(C)C)cc1]

It is also known as Ecamsule. This is commercially available as Mexoryl SX (U.S. Pat. No. 4,585,597) by L'Oreal or Sunsafe TDSA (from Uniproma). It can be used as parent acid or its salts to deliver the desired benefit.

The composition comprises 0.1 to 10 wt %, preferably 0.25 to 8 wt %, more preferably 0.5 to 5 wt % water soluble UVA sunscreen. The composition comprises 0.1 to 10 wt %, preferably 0.25 to 8 wt %, more preferably 0.5 to 5 wt % water soluble UVB sunscreen.

The water-soluble sunscreens for inclusion in the composition of the present invention are generally commercially available in the acid form. When included in the composition in the acid form (pre neutralized forms) i.e having sulphonic acid group (—$SO_3H$) the composition additionally comprises a neutralising agent to convert the acid form in to the salt form, in which form it is known to be active as a sunscreen with an exception to Mexoryl SX which can act as sunscreen with and without neutralization. When included, the neutralising agent is preferably included in an amount 0.05 to 4 wt % in the composition. The neutralising agent is preferably an inorganic or an organic alkali. Organic alkali is preferably an amine such as triethanol amine or diethanol amine. The present inventors have observed that the inorganic alkali is especially preferred. Preferred are alkali metal hydroxides. Most preferred metal hydroxide for inclusion as neutralising agent in the composition of the invention are sodium hydroxide or potassium hydroxide.

Without wishing to be bound by theory, the inventors believe that adding only UVB sunscreen alone would not provide complete erythema protection as well as UV protection and deposition of a single water soluble UVB sunscreen active can saturate at one concentration point on the skin surface, but this limitation can be exceeded with select combination of sunscreens chosen by their structure and solubility which determine their partition between rinse away water and cleansing surface resulting in higher sunscreen deposition and enhanced SPF benefits.

The composition of the invention comprises a surfactant which aids in the cleaning action. To enable cleaning, surfactant is included in 3 to 80 wt % preferably 6 to 80 wt %, further more preferably 10 to 75 wt % in the composition.

Skin Cleansing Compositions

The surfactant is preferably an anionic surfactant e.g. an alkyl sulphate and/or ethoxylated alkyl sulfate surfactant. These anionic surfactants are preferably present at a level of from 1 to 20 wt %, preferably 2 to 16 wt %, further more preferably from 3 to 16 wt % in the composition. Preferred alkyl sulfates are C8-18 alky sulfates, more preferably C12-18 alkyl sulfates, preferably in the form of a salt with a solubilising cation such as sodium, potassium, ammonium or substituted ammonium. Preferred alkyl ether sulfates are those having the formula: $RO(CH_2CH_2O)_nSO_3M$; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilising cation such as sodium, potassium, ammonium or substituted ammonium. An example is sodium lauryl ether sulfate (SLES). SLES having an average degree of ethoxylation of from 0.5 to 3, preferably 1 to 3 is especially preferred. The composition may comprise one or more further anionic cleansing surfactants which are cosmetically acceptable and suitable for topical application.

The composition of the invention preferably additionally comprises an amphoteric surfactant preferably a betaine surfactant preferably an alkyl amidopropyl betaine surfactant for example cocamidopropyl betaine (CAPB). In a preferred embodiment, the composition comprises from 0.1 to 10 wt. %, preferably from 0.5 to 8 wt. %, more preferably from 1 to 5 wt. % of a betaine surfactant SLES and CAPB are often combined for use in shampoo and bodywash compositions. Alternately the composition may be formulated as a soap bar or liquid soap bodywash.

Soap is a suitable surfactant for personal washing applications of composition of the invention. The soap is preferably C8-C24 soap, more preferably C10-C20 soap and most preferably C12-C16 soap. The soap may or may not have one or more carbon-carbon double bond or triple bond. The cation of the soap may be alkali metal, alkaline earth metal or ammonium. Preferably, the cation of the soap is selected from sodium, potassium or ammonium. More preferably the cation of the soap is sodium or potassium.

The soap may be obtained by saponifying a fat and/or a fatty acid. The fats or oils generally used in soap manufacture may be such as tallow, tallow stearines, palm oil, palm stearines, soya bean oil, fish oil, castor oil, rice bran oil, sunflower oil, coconut oil, babassu oil, palm kernel oil, and others. In the above process the fatty acids are derived from oils/fats selected from coconut, rice bran, groundnut, tallow, palm, palm kernel, cotton seed, soyabean, castor etc.

A typical fatty acid blend consisted of 5 to 30% coconut fatty acids and 70 to 95% fatty acids ex hardened rice bran oil. Fatty acids derived from other suitable oils/fats such as groundnut, soybean, tallow, palm, palm kernel, etc. may also be used in other desired proportions. The most preferred soap is a laurate soap. The soap, when present in solid forms of the present invention is present in an amount of 30 to 90 wt %, preferably from 50 to 85 wt %, more preferably 55 to 75 wt %. The soap, when present in liquid forms of the composition is present in 0.5 to 20 wt %, preferably from 1 to 10 wt %.

Alternatively the surfactants are non-ionic surfactants, such as C8-C22, preferably C8-C16 fatty alcohol ethoxylates, comprising between 1 and 8 ethylene oxide the surfactants are preferably selected from primary alkyl sulphate, secondary alkyl sulphonates, alkyl benzene sulphonates, or ethoxylated alkyl sulphates. Alkyl polyglucoside may also be present in the composition, preferably those having a carbon chain length between C6 and C16. Suitable surfactant concentrations in liquid forms of cleaning application are generally more than 0.5 but less than 30 wt %, preferably from 1 to 20 wt %. In solid compositions, the surfactant is preferably present in 30 to 80 wt %, preferably from 50 to 80 wt %.

The composition of the invention comprises a cosmetically acceptable carrier. The cosmetically acceptable carrier is preferably an aqueous solution/dispersion of cosmetically acceptable adjuvents. Water is generally included in the composition of the invention. When the composition is in solid form e.g. in the form of a soap bar, the amount of water is in the range 14 to 25 wt %, preferably 15 to 22 wt %. When the composition is formulated in liquid, emulsion or gel form, the water content is generally in the range of 50 to 95 wt %, preferably in the range of 60 to 85 wt %.

Additional adjuvents which may be used to make up the cosmetically acceptable carrier of the skin cleansing composition of the invention are described below.

When made as a soap bar composition it may optionally comprise 2 to 15 wt %, preferably 4 to 12 wt % free fatty acids. By free fatty acids is meant a carboxylic acid comprising a hydrocarbon chain and a terminal carboxyl group bonded to an H. Suitable fatty acids are C8 to C22 fatty acids. Preferred fatty acids are C12 to C18, preferably predominantly saturated, straight-chain fatty acids. However, some unsaturated fatty acids or hydroxylated saturated fatty acid such as 12 Hydroxy stearic acid can also be employed.

In the form of a soap bar, the composition generally comprises electrolyte. Electrolytes as per this invention include compounds that substantially dissociate into ions in water. Suitable electrolytes for inclusion in the soap making process are alkali metal salts. Preferred alkali metal salts include sodium sulfate, sodium chloride, sodium acetate, sodium citrate, potassium chloride, potassium sulfate, sodium carbonate and other mono or di or tri salts of alkaline earth metals, more preferred electrolytes are sodium chloride, sodium sulfate, sodium citrate, potassium chloride and especially preferred electrolyte is sodium chloride, sodium sulphate, sodium citrate or a combination thereof. Electrolyte is preferably included in the composition in an amount 0.1 to 6 wt %, more preferably 0.5 to 6 wt %, even more preferably 0.5 to 5 wt %, further more preferably 0.5 to 3 wt %, and most preferably 1 to 3 wt %.

The composition preferably comprises a polyhydric alcohol (also called polyol) or mixture of polyols. Polyol is a term used herein to designate a compound having multiple hydroxyl groups (at least two, preferably at least three) which is highly water soluble. Many types of polyols are available including: relatively low molecular weight short chain polyhydroxy compounds such as glycerol and propylene glycol; sugars such as sorbitol, manitol, sucrose and glucose; modified carbohydrates such as hydrolyzed starch, dextrin and maltodextrin, and polymeric synthetic polyols such as polyalkylene glycols, for example polyoxyethylene glycol (PEG) and polyoxypropylene glycol (PPG). Especially preferred polyols are glycerol, sorbitol and their mixtures. Most preferred polyol is glycerol. In a preferred embodiment, the bars of the invention comprise 0 to 8 wt %, preferably 1 to 7.5 wt % by wt. polyol.

Suitable starchy materials which may be used include natural starch (from corn, wheat, rice, potato, tapioca and the like), pregelatinzed starch, various physically and chemically modified starch and mixtures thereof. By the term natural starch is meant starch which has not been subjected to chemical or physical modification—also known as raw or native starch. The raw starch can be used directly or modified during the process of making the bar composition such that the starch becomes gelatinized, either partially or fully gelatinized.

The adjuvant system may optionally include insoluble particles comprising one or a combination of materials. By insoluble particles is meant materials that are present in solid particulate form and suitable for personal washing. Preferably, there are mineral (e.g., inorganic) or organic particles.

The insoluble particles should not be perceived as scratchy or granular and thus should have a particle size less than 300 microns, more preferably less than 100 microns and most preferably less than 50 microns.

Preferred inorganic particulate material includes talc and calcium carbonate. Talc is a magnesium silicate mineral material, with a sheet silicate structure and a composition of $Mg_3Si_4(OH)_{22}$, and may be available in the hydrated form. It has a plate-like morphology, and is essentially oleophilic/hydrophobic, i.e., it is wetted by oil rather than water.

Calcium carbonate or chalk exists in three crystal forms: calcite, aragonite and vaterite. The natural morphology of calcite is rhombohedral or cuboidal, acicular or dendritic for aragonite and spheroidal for vaterite.

Examples of other optional insoluble inorganic particulate materials include aluminates, silicates, phosphates, insoluble sulfates, borates and clays (e.g., kaolin, china clay) and their combinations.

Organic particulate materials include insoluble polysaccharides such as highly crosslinked or insolubilized starch (e.g., by reaction with a hydrophobe such as octyl succinate) and cellulose; synthetic polymers such as various polymer lattices and suspension polymers; insoluble soaps and mixtures thereof.

It is preferred that the compositions of the invention comprise polymers. Polymers of the acrylate class are especially preferred. Preferred bars include 0.05 to 5 wt % acrylates. More preferred bars include 0.01 to 3 wt % acrylates. Examples of acrylate polymers include polymers and copolymers of acrylic acid crosslinked with polyallylsucrose as described in U.S. Pat. No. 2,798,053 which is herein incorporated by reference. Other examples include polyacrylates, acrylate copolymers or alkali swellable emulsion acrylate copolymers, hydrophobically modified alkali swellable copolymers, and crosslinked homopolymers of acrylic acid. Examples of such commercially available polymers are: ACULYN®, CARBOPOL®, and CARBOPOL® Ultrez grade series.

Bar compositions preferably comprise 0.1 to 25 wt %, preferably 5 to 15 wt % of these mineral or organic particles.

An opacifier may be optionally present in the personal care composition. When opacifiers are present, the cleansing bar is generally opaque. Examples of opacifiers include titanium dioxide, zinc oxide and the like. A particularly preferred opacifier that can be employed when an opaque soap composition is desired is ethylene glycol mono- or di-stearate, for example in the form of a 20% solution in sodium lauryl ether sulphate. An alternative opacifying agent is zinc stearate.

The product can take the form of a water-clear, i.e. transparent soap, in which case it will not contain an opacifier.

The pH of preferred soaps bars of the invention is from 8 to 11, more preferably 9 to 11. Products in the liquid form which generally comprises synthetic surfactants preferably have a pH of 6 to 8.

A preferred composition may additionally include up to 30 wt % benefit agents. Preferred benefit agents include moisturizers, emollients, sunscreens and anti-ageing compounds. The agents may be added at an appropriate step during the process of making the bars. Some benefit agents may be introduced as macro domains.

Other optional ingredients like anti-oxidants, perfumes, polymers, chelating agents, colourants, deodorants, dyes, enzymes, foam boosters, germicides, anti-microbials, lathering agents, pearlescers, skin conditioners, stabilizers or superfatting agents, may be added in suitable amounts in the process of the invention. Preferably, the ingredients are added after the saponification step. Sodium metabisulphite, ethylene diamine tetra acetic acid (EDTA), borax or ethylene hydroxy diphosphonic acid (EHDP) are preferably added to the composition.

The composition of the invention could be used to deliver antimicrobial benefits. Antimicrobial agents that are preferably included to deliver this benefits include oligodynamic metals or compounds thereof. Preferred metals are silver, copper, zinc, gold or aluminium. Silver is particularly preferred. In the ionic form it may exist as a salt or any compound in any applicable oxidation state. Preferred silver compounds are silver oxide, silver nitrate, silver acetate, silver sulfate, silver benzoate, silver salicylate, silver carbonate, silver citrate or silver phosphate, with silver oxide, silver sulfate and silver citrate being of particular interest in one or more embodiments. In at least one preferred embodiment the silver compound is silver oxide. Oligodynamic metal or a compound thereof is preferably included in 0.0001 to 2 wt %, preferably 0.001 to 1 wt % in the composition. Alternately an essential oil antimicrobial active may be included in the composition of the invention. Preferred essential oil actives which may be included are terpineol, thymol, carvacol, (E)-2(prop-1-enyl) phenol, 2-propylphenol, 4-pentylphenol, 4-sec-butylphenol, 2-benzyl phenol, eugenol or combinations thereof. Further more preferred essential oil actives are terpineol, thymol, carvacrol or thymol, most preferred being terpineol or thymol and ideally a combination of the two. Essential oil actives are preferably included in 0.001 to 1 wt %, preferably 0.01 to 0.5 wt % in the composition.

Hair Care Compositions: Shampoos and Conditioners:

As per another aspect of the invention, the composition may be used for hair care. One medium for hair cleansing and care is a shampoo. The shampoo compositions of the invention are generally formulated with an anionic surfactant e.g. an alkyl sulphate and/or ethoxylated alkyl sulfate surfactant. These anionic surfactants are preferably present at a level of from 1 to 20 wt %, preferably 2 to 16 wt %, further more preferably from 3 to 16 wt % in the composition. Preferred alkyl sulfates are C8-18 alky sulfates, more preferably C12-18 alkyl sulfates, preferably in the form of a salt with a solubilising cation such as sodium, potassium, ammonium or substituted ammonium.

Preferred alkyl ether sulfates are those having the formula: $RO(CH_2CH_2O)_nSO_3M$;
wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilising cation such as sodium, potassium, ammonium or substituted ammonium. An example is sodium lauryl ether sulfate (SLES).

Preferred ethoxylated alkyl sulfate anionic surfactant is sodium lauryl ether sulfate (SLES). SLES having an average degree of ethoxylation of from 0.5 to 3, preferably 1 to 3 is especially preferred.

Shampoo compositions according to the invention may comprise one or more further anionic cleansing surfactants which are cosmetically acceptable and suitable for topical application to the hair.

A composition of the invention preferably additionally comprises an amphoteric surfactant preferably a betaine surfactant preferably an alkyl amidopropyl betaine surfactant for example cocamidopropyl betaine. In a preferred embodiment, the composition comprises from 0.1 to 10 wt %, preferably from 0.5 to 8 wt %, more preferably from 1 to 5 wt % of a betaine surfactant.

To enhance deposition of actives from compositions of the invention especially shampoos, cationic polymers are generally included therein. In the present invention too, it is preferred that the composition additionally includes 0.01 to 2.0 wt % of a cationic polymer. The cationic polymer is preferably guar hydroxypropyl trimonium chloride. Guar polymer predominantly contains galactomannan polymer chains. This polymer is available at various molecular weights and degree of cationic substitutions depending on how much the guar has been hydrolysed and cationised. The cationic polymer is preferably present in 0.04 to 0.5 wt %, more preferably 0.08 to 0.25 wt % in the composition.

When conditioning benefits are to be delivered through the composition of the invention the composition is called a hair conditioner. Typically, the most popular conditioning agents used in hair care compositions are water-insoluble oily materials such as mineral oils, naturally occurring oils such as triglycerides and silicone polymers. Conditioning benefit is achieved by the oily material being deposited onto the hair resulting in the formation of a film, which makes the hair easier to comb when wet and more manageable when dry. An especially useful conditioning agent is a silicone compound, preferably a non-volatile silicone compound. Advantageously compositions herein may include one or more silicones. The silicones are conditioning agents found in dispersed or suspended particulate form. They are intended to deposit onto hair remaining behind after rinsing of the hair with water. Suitable silicone oils may include polyalkyl siloxanes, polyaryl siloxanes, polyalkylaryl siloxanes, polyether siloxane copolymers and mixtures thereof. Amino silicones are often formulated with shampoo compositions. Amino silicones are silicones containing at least one primary amine, secondary amine, tertiary amine or a quaternary ammonium group. High molecular weight silicone gums can also be utilized. Another useful type are the crosslinked silicone elastomers such as Dimethicone/Vinyl/Dimethicone Crosspolymers (e.g. Dow Corning 9040 and 9041).

Amounts of the silicone in compositions where present may range from about 0.1 to about 10 wt %, preferably from about 0.1 to about 8 wt %, more preferably from about 0.3 to about 5 wt % in the hair care compositions.

The pH of the composition is preferably equal to or higher than 4.0, more preferably in the range of 5.0 to 7.0.

The hair conditioning composition usually comprises conditioning surfactants selected from cationic surfactants, used singly or in admixture. Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant. Yet another preferred cationic surfactant is stearamidopropyl dimethylamine.

The most preferred cationic surfactants for use in the composition are stearamidopropyl dimethylamine, behentrimonium chloride, or stearyl trimethyl ammonium chloride. In conditioners of the invention, the level of cationic surfactant will generally range from 0.1 to 5 wt %, preferably 0.5 to 2.5 wt %.

Hair conditioning compositions of the invention preferably may also additionally comprise a fatty alcohol. The combined use of fatty alcohols and cationic surfactants in conditioning compositions is believed to be especially advantageous, because this leads to the formation of a lamellar phase, in which the cationic surfactant is dispersed.

Hair care compositions whether delivered as shampoos or conditioners usually comprise an anti-dandruff agent. The most preferred anti-dandruff agent for use in the compositon of the invention is a zinc based anti-dandruff agent preferably zinc pyrthione. Shampoo composition as per the invention preferably additionally or alternately comprises a conazole fungicide. Preferably the conazole fungicide is selected form ketoconazole, climbazole or mixtures thereof. The azole fungicide is preferably included in 0.01 to 2 wt %, more preferably 0.025 to 0.75 wt % in the composition. The presence of a conazole fungicide is believed to improve the deposition of zinc pyrithione.

The invention also relates to a method of providing improved sun protection factor to a topical surface of the body from a wash off composition comprising the steps of:
(a) washing the surface with a composition of the first aspect, preferably diluted with water; and
(b) rinsing the surface with water,
wherein the sun protection factor is at least 8.

Preferably, the sun protection factor is obtained by the method is at least 10.

When diluted, water at 1 to 20 times of the amount of the composition may be used. The surface may thereafter be rinsed using copious amount of water to make it substantially free of the surfactant in the composition.

In a third aspect, the present invention also relates to use of the composition for obtaining sun protection factor of at least 8, preferably at least 10.

The invention will now be demonstrated with the help of the following non-limiting examples.

EXAMPLES

Examples A-C, 1,2: Interaction of Sunscreens as Per the Invention to Provide Synergistic SPF Benefits The compositions as given in Table-1 below were prepared. The in vitro-SPF of the compositions was measured using the procedure given below.

Diluted compositions as shown in Table-1 were applied on pre-wet vitro skin. These vitro skin samples were then rinsed off immediately post the product application and kept in a dark room for drying. After drying, the vitro skin samples was exposed to UV light and the transmittance scan was recorded using Labsphere UV-2000S Ultraviolet Transmittance Analyzer. This scan gives the transmittance as a function of wavelength (290-400 nm) for a given sample. For a single vitro skin sample four different spots were scanned. The same was repeated for 3 vitro skin samples. The data reported is thus an average of 12 readings. The reference transmittance scan was obtained using blank vitro skin, with glycerine spread on it as control. The transmittance values were used to arrive at the SPF values using the software provided with the instrument. The SPF value obtained as an average of 12 readings measured over 3 vitro skin samples are given in Table-1 below:

TABLE 1

| Ingredients (wt %) | A | B | C | 1 | 2 |
|---|---|---|---|---|---|
| SLES | 12.0 | 12.0 | 12.0 | 12.0 | 12.0 |
| CAPB (30%) | 13.4 | 13.4 | 13.4 | 13.4 | 13.4 |
| TDSA | 1.2 | — | — | 1.2 | — |
| PBSA | — | 3.0 | — | 3.0 | 3.0 |
| Neoheliopan AP | — | — | 1.2 | — | 1.2 |
| Glycerol | 2.0 | 2.0 | 2.0 | 2.0 | 2.0 |
| KOH (84%) | 0.29 | 0.77 | 0.24 | 1.06 | 1.01 |
| Water | To 100 | To 100 | To 100 | To 100 | To 100 |
| SPF | 1.9 ± 0.1 | 7.6 ± 0.25 | 2 ± 0.1 | 12.3 ± 1.44 | 16.0 ± 1.4 |

The data in the table-1 above indicates that the compositions as per the invention (Examples 1 and 2) provide for synergistic SPF values over those exhibited by the individual components alone (Examples A-C).

Example D,3: % UV Protection as Per the Invention as Compared to Composition Outside the Invention Compositions as shown in Table-2 below were prepared. The % UV protection was measured for the compositions therein using the following procedure:

The compositions were diluted with water and then applied on to pre-wet vitro skin. The vitro skin was then rinsed off immediately post product application and kept for drying in the dark. After drying, the vitro skin was exposed to UV light and transmittance scan was recorded. This scan gives the transmittance as a function of wavelength (290-400 nm) for a given sample. For a single vitro skin sample four different spots were scanned. The same was repeated for 3 vitro skin samples. The data reported is thus an average of 12 readings. The reference transmittance scan was obtained using blank vitro skin, with glycerine spread on it as control. The transmittance values were recorded using UV-2000S Ultraviolet Transmittance Analyzer and transmittance data extracted using UV-2000S application software provided with the instrument.

Percentage Protection Calculation:

Percentage protection for each vitro skin sample was calculated by Area under the curve calculation method (using Trapezoid equation).

TABLE 2

| Ingredients (wt %) | D | 3 |
|---|---|---|
| SLES | 12.0 | 12.0 |
| CAPB (30%) | 13.4 | 13.4 |
| PBSA | 4.2 | 3.0 |
| Neoheliopan AP | — | 1.2 |
| Glycerol | 2.0 | 2.0 |
| KOH (84%) | 1.07 | 1.06 |
| Water | To 100 | To 100 |
| % UV protection | 31.0 ± 0.5 | 61.3 ± 3.2 |

The data in Table-2 above confirms that the composition as per the invention (Example-3) which comprises both a water soluble sunscreen of the UVA type and a water soluble sunscreen of the UVB type is far superior to a composition comprising only one type of water soluble sunscreen (Example-D), at the same total sunscreen concentration.

Examples E, F: SPF Obtained Using Benzophenone-4 as the Only Sunscreen

The SPF of the compositions shown in table-3 below was measured as described for examples in table-1 above.

TABLE 3

| Ingredients (wt %) | E | F |
|---|---|---|
| SLES | 12 | 12 |
| CAPB (30%) | 13.4 | 13.4 |
| TDSA | — | — |
| PBSA | — | — |
| Neoheliopan AP | — | — |
| Benzophenone-4 | 1.2 | 3 |
| Glycerol | 2 | 2 |
| KOH (85%) | 0.27 | 0.68 |

TABLE 3-continued

| Ingredients (wt %) | E | F |
|---|---|---|
| Water | to 100 | to 100 |
| In vitro SPF | 2.01 ± 0.08 | 4.85 ± 0.78 |

The invention claimed is:

1. A personal cleansing composition for enhanced deposition of sunscreens on a topical surface of the body comprising:
    (a) 0.1 to 10 wt % of a water soluble UVA sunscreen;
    (b) 0.1 to 10 wt % of a water soluble UVB sunscreen;
    (c) 3 to 80 wt % surfactant; and
    (d) a cosmetically acceptable carrier,
    wherein the water soluble UVA sunscreen is selected from di sodium phenyl dibenzimidazole tetra sulfonate, terephthalylidene dicamphor sulfonic acid and mixtures thereof, and
    wherein the water soluble UVB sunscreen is selected from phenyl benzimidazole sulphonic acid, benzylidene camphor sulfonic acid, benzophenone-4 and mixtures thereof, and
    wherein the solubility in water of said UVA sunscreen and said UVB sunscreen is higher than 10 g/L at 25° C.

2. The personal cleansing composition as claimed in claim 1, wherein the UVB sunscreen is selected from phenyl benzimidazole sulphonic acid, benzylidene camphor sulfonic acid and mixtures thereof.

3. The personal cleansing composition as claimed in claim 1, further comprising 0.05 to 4 wt % neutralising agent.

4. The personal cleansing composition as claimed in claim 3, wherein the neutralising agent is an inorganic or organic alkali.

5. The personal cleansing composition as claimed in claim 1, comprising 10 to 75 wt % surfactant.

6. A method of providing improved sun protection factor to a topical surface of the body from a wash off composition comprising the steps of:
    (a) washing the surface with the personal cleansing composition as claimed in claim 1; and
    (b) rinsing said surface with water,
    wherein the sun protection factor is at least 8.

7. The method as claimed in claim 6, wherein the personal cleansing composition is diluted with water.

8. The personal cleansing composition as claimed in claim 1, wherein the personal cleansing composition is a rinse-off composition.

* * * * *